United States Patent
Shekhar et al.

(10) Patent No.: US 10,071,938 B2
(45) Date of Patent: Sep. 11, 2018

(54) HYDROCARBON DEHYDROCYCLIZATION

(71) Applicant: ExxonMobil Chemical Patents Inc., Baytown, TX (US)

(72) Inventors: Mayank Shekhar, Houston, TX (US); Paul F. Keusenkothen, Houston, TX (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 36 days.

(21) Appl. No.: 15/240,829

(22) Filed: Aug. 18, 2016

(65) Prior Publication Data

US 2017/0088488 A1 Mar. 30, 2017

Related U.S. Application Data

(60) Provisional application No. 62/232,609, filed on Sep. 25, 2015, provisional application No. 62/313,288, filed on Mar. 25, 2016.

(30) Foreign Application Priority Data

Nov. 19, 2015 (EP) .................................... 15195311
Jun. 8, 2016 (EP) .................................... 16173587

(51) Int. Cl.
*C07C 2/76* (2006.01)
*B01J 29/40* (2006.01)

(52) U.S. Cl.
CPC ................. *C07C 2/76* (2013.01); *B01J 29/40* (2013.01); *C07C 2529/40* (2013.01); *Y02P 20/52* (2015.11)

(58) Field of Classification Search
CPC combination set(s) only.
See application file for complete search history.

(56) References Cited

U.S. PATENT DOCUMENTS

| | | | |
|---|---|---|---|
| 4,751,338 | A | 6/1988 | Tabak et al. |
| 4,855,522 | A | 8/1989 | Diaz |
| 5,026,937 | A | 6/1991 | Bricker |
| 5,633,417 | A | 5/1997 | Beck et al. |
| 5,675,047 | A | 10/1997 | Beck et al. |
| 5,936,135 | A | 8/1999 | Choudhary et al. |
| 6,642,426 | B1 | 11/2003 | Johnson et al. |
| 6,670,517 | B1 | 12/2003 | Abichandani et al. |
| 8,692,043 | B2 | 4/2014 | Lauritzen et al. |
| 8,835,706 | B2 * | 9/2014 | Iyer .......................... C07C 2/76 585/301 |
| 9,144,790 | B2 | 9/2015 | Lauritzen et al. |
| 2009/0030253 | A1 | 1/2009 | Xu et al. |
| 2009/0209794 | A1 | 8/2009 | Lauritzen et al. |
| 2014/0256536 | A1 | 9/2014 | Lauritzen et al. |
| 2015/0376088 | A1 | 12/2015 | Molinier et al. |

* cited by examiner

*Primary Examiner* — Tam M Nguyen (57) ABSTRACT

The invention relates to the production of aromatic hydrocarbon by the conversion of a feed comprising $C_{2+}$ non-aromatic hydrocarbon, e.g., natural gas. The invention is particularly useful in converting natural gas to liquid-phase aromatic hydrocarbon, which can be more easily transported away from remote natural gas production facilities. The conversion is carried out in the presence of a dehydrocyclization catalyst comprising dehydrogenation and molecular sieve components. The dehydrocyclization catalyst has an average residence time of 90 seconds or less.

25 Claims, 2 Drawing Sheets

HYDROCARBON DEHYDROCYCLIZATION

CROSS-REFERENCE TO RELATED APPLICATIONS

This invention claims priority to and the benefit of U.S. Patent Application Ser. No. 62/232,609 filed Sep. 25, 2015, U.S. Patent Application Ser. No. 62/313,288, filed Mar. 25, 2016, European Patent Application No. 15195311.4 filed Nov. 19, 2015, and European Patent Application No. 16173587.3, filed Jun. 8, 2016, all of which are incorporated by reference in their entireties. The following related cases are also incorporated by reference in their entireties: U.S. Patent Application Ser. No. 62/234,262; European Patent Application No. 15195314.8; U.S. Patent Application Ser. No. 62/234,240; European Patent Application No. 15197698.2; U.S. Patent Application Ser. No. 62/247,795; European Patent Application No. 15197700.6; U.S. Patent Application Ser. No. 62/248,374; European Patent Application No. 15197702.2; U.S. Patent Application Ser. No. 62/253,268; U.S. Patent Application Ser. No. 62/298,655; European Patent Application No. 16167672.1; U.S. Patent Application Ser. No. 62/326,918; European Patent Application No. 16175163.1; U.S. Patent Application Ser. No. 62/299,730; European Patent Application No. 16167395.9; U.S. Patent Application Ser. No. 62/313,306 and European Patent Application No. 16173980.0.

FIELD

The invention relates to the production of aromatic hydrocarbon by the conversion of a feed comprising $C_{2+}$ non-aromatic hydrocarbon. The conversion is carried out in the presence of a dehydrocyclization catalyst comprising dehydrogenation and molecular sieve components. The dehydrocyclization catalyst has an average residence time of 90 seconds or less.

BACKGROUND

Aromatic hydrocarbon compounds such as benzene are frequently used for producing transportation fuels and petrochemicals such as styrene, phenol, nylon, polyurethanes and many others. Benzene can be produced, e.g., by steam cracking and naphtha reforming. During steam cracking, a $C_{2+}$ hydrocarbon feed reacts in the presence of steam under high-temperature pyrolysis conditions to produce a product comprising molecular hydrogen, $C_{4-}$ olefin, other $C_{4-}$ hydrocarbon, and $C_{5+}$ hydrocarbon. The yield of aromatic hydrocarbon from steam cracking is generally much less than the yield of light hydrocarbon, and processes of significant complexity are typically needed for aromatics separation and recovery. Naphtha reforming catalytically produces a product having a much greater content of aromatic hydrocarbon than does steam cracker effluent, but the naphtha feed is itself useful for other purposes such as motor gasoline blendstock.

Attempts have been made to overcome these difficulties, and provide an efficient process for producing aromatic hydrocarbon at high yield from a relatively inexpensive feed. For example, processes have been developed for producing light aromatic hydrocarbon (e.g., benzene, toluene, and xylenes—"BTX") from paraffinic $C_1$-$C_4$ feeds. The processes typically utilize a catalyst having a molecular sieve component e.g., ZSM-5, and a dehydrogenation component, such as one or more of Pt, Ga, Zn, and Mo. These conventional processes typically operate at high temperature and low pressure. Although these conditions increase the yield of aromatic hydrocarbon, they also lead to an increased rate of catalyst deactivation, mainly resulting from increased catalyst coking.

One way to lessen the amount of catalyst coking involves increasing the relative amount of methane in the feed, as disclosed in U.S. Pat. No. 5,026,937. Relative methane content can be increased by removing $C_{2+}$ hydrocarbon from the feed. Since ethane, propane, and butanes are less refractory than methane, removing these compounds from the feed decreases the amount of over-cracking, and lessens the accumulation of catalyst coke.

Aromatization processes having a decreased selectivity for catalyst coke have also been developed. For example, U.S. Pat. No. 4,855,522 discloses using a dehydrocyclization catalyst comprising (a) an aluminosilicate having a silica:alumina molar ratio of at least 5 and (b) a compound of (i) Ga and (ii) at least one rare earth metal. The aromatization is carried out at a temperature ≥450° C., (e.g., 475° C., to 650° C.) and a pressure of from 1 bar to 20 bar. Other processes limit decrease selectivity for catalyst coke by carrying out the reaction for a relatively short time (e.g., less than a day), and then halting the reaction so that the catalyst can be regenerated. For example, U.S. Patent Application Publication No. 2009/0209794 A1, and U.S. Pat. Nos. 8,692,043 and 9,144,790 disclose a process for aromatizing lower alkanes using a particulate catalyst, where the catalyst particles have an average catalyst particle residence time in the reaction zone in the range of about 0.1 second to about 30 minutes. According to those references, such a residence time can be achieved by carrying out the aromatization in a fluid bed, and continuously withdrawing catalyst from the bed for regeneration. Maximum ethane conversion is about 63%, and the catalyst and process conditions which achieve appreciable ethane conversion also exhibit appreciable selectivity for methane.

It is desired to produce aromatic hydrocarbon from $C_{2+}$ non-aromatic hydrocarbon at greater feed conversion, particularly with less methane yield. Processes which operate at a space velocity (GHSV) greater than 1000 $hr^{-1}$ are particularly desired.

SUMMARY

Catalytic processes for aromatizing substantially non-aromatic $C_{2+}$ hydrocarbon have been developed which feature greater feed conversion and typically less methane selectivity than conventional aromatization processes. It has been discovered that a feed conversion greater than 65 wt. % can be achieved, even with relatively refractory feeds such as ethane, when the average residence time of the catalyst in the reaction zone under reaction conditions is about 90 seconds or less.

Accordingly, certain aspects the of invention relate to a process for producing aromatic hydrocarbon from a feed comprising ≥1 wt. % of $C_{2+}$ non-aromatic hydrocarbon. The process utilizes at least one catalyst having catalytic activity for dehydrocyclization of the feed's $C_{2+}$ non-aromatic hydrocarbon. The catalyst includes a molecular sieve component and a dehydrogenation component. The process is carried out under reaction conditions which include a temperature in the range of from 400° C. to 800° C., a pressure in the range of from 0 psig (101 kPa) to 300 psig (2170 kPa), wherein the average residence time of the catalyst in the reaction zone under the reaction conditions is ≤90 seconds. Under these conditions, ≥65 wt. % of the feed's $C_{2+}$ non-aromatic hydrocarbon is converted to a product comprising ≥1 wt. % of aromatic hydrocarbon. The process also includes recovering at least a portion of the product's aromatic hydrocarbon.

It has also been found that decreasing the catalyst's average residence time in the reaction zone under the reaction conditions to duration of 90 seconds or less increases conversion of the feed's non-aromatic hydrocarbon without significantly increasing methane selectivity. This feature is useful for natural gas dehydrocyclization, and especially so when the dehydrocyclization is carried out at a relatively large space velocity.

Accordingly, other aspects of the invention relate to a process for upgrading a feed which includes ≥50 wt. % of a natural gas which comprises $C_2$-$C_4$ paraffinic hydrocarbon. The process includes reacting the feed under dehydrocyclization conditions in the presence of a dehydrocyclization catalyst which comprises ≥25 wt. % of a molecular sieve component and ≥0.05 wt. % of a dehydrogenation component. The molecular sieve component comprises ≥90 wt. % of one or more of MCM-22, ZSM-5, ZSM-11, ZSM-12, ZSM-22, ZSM-23, ZSM-35, and ZSM-48. The dehydrogenation component comprises ≥90 wt. % of one or more of Ga, Zn, Cu, Re, Mo, W, La, Fe, Ag, Pt, and Pd. The dehydrocyclization conditions include a temperature in the range of from 400° C. to 800° C., a pressure in the range of from 0 psig (101 kPa) to 300 psig (2170 kPa), and a space velocity ("GHSV", volume of feed per volume of catalyst per hour)≥1100 hr$^{-1}$. Feed volume under reaction conditions can be approximated from the feed's equation of state. Catalyst volume, e.g., catalyst bed volume, is equal to average catalyst mass divided by average catalyst density, e.g., the average mass density of a catalyst in a catalyst bed. The dehydrocyclization catalyst has an average residence time in the reaction zone under the dehydrocyclization conditions of ≤90 seconds. The process achieves a conversion of ≥65 wt. % of the feed's $C_2$-$C_4$ paraffinic hydrocarbon. As in the previous aspects, the process also includes recovering at least a portion of the product's aromatic hydrocarbon.

It has also been found that carrying out the catalytic dehydrocyclization of a substantially non-aromatic $C_{2+}$ hydrocarbon feed with a dehydrocyclization catalyst having an average residence time in the reaction zone under the dehydrocyclization conditions that is ≤90 seconds achieves a decrease in methane selectivity, compared to conventional processes, over a very wide range feed conversion. Desirably, this feature is observed even for dehydrocyclization catalysts which are substantially free of platinum.

Accordingly, other aspects of the invention relate to processes for producing aromatic hydrocarbon from feeds comprising ≥1 wt. % of $C_{2+}$ non-aromatic hydrocarbon. The process is carried out in a reaction zone which includes catalyst having catalytic activity for dehydrocyclization. The feed is reacted in the presence of the catalyst under dehydrocyclization conditions to produce a product comprising methane and ≥1 wt. % of aromatic hydrocarbon. The dehydrocyclization is carried out under conditions include a temperature in the range of from 400° C. to 800° C., a pressure in the range of from 0 psig (101 kPa) to 300 psig (2170 kPa), a space velocity (GHSV)≥1100 hr$^{-1}$, wherein dehydrocyclization catalyst has an average residence time in the reaction zone under the dehydrocyclization conditions of ≤90 seconds. The process includes recovering at least a portion of the product's aromatic hydrocarbon. When carried out under the specified conditions, the reaction achieves (A) a $C_{2+}$ conversion of X wt. % and (B) a methane selectivity of Y wt. %, wherein when (A) X>60, then Y≤40, (B) X is in the range of 50 to 60 then Y≤20, and (C) X<50 then Y≤15.

Still other aspects of the invention relate to systems and catalysts that can be used for carrying out one or more of the preceding aspects.

DETAILED DESCRIPTION

The invention relates to producing aromatics by the catalytic dehydrocyclization of a substantially non-aromatic $C_{2+}$ hydrocarbon, the dehydrocyclization catalyst having an average residence time in the reaction zone under the dehydrocyclization conditions of ≤90 seconds. The catalyst includes a molecular sieve component and a dehydrogenation component. For the purpose of this description and dependent claims, the following terms are defined.

The term "$C_n$" hydrocarbon means hydrocarbon having n carbon atom(s) per molecule, wherein n is a positive integer. The term "$C_{n+}$" hydrocarbon means hydrocarbon having at least n carbon atom(s) per molecule. The term "$C_{n-}$" hydrocarbon means hydrocarbon having no more than n carbon atom(s) per molecule. The term "hydrocarbon" means a class of compounds containing hydrogen bound to carbon, and encompasses (i) saturated hydrocarbon, (ii) unsaturated hydrocarbon, and (iii) mixtures of hydrocarbons, and including mixtures of hydrocarbon compounds (saturated and/or unsaturated), such as mixtures of hydrocarbon compounds having different values of n.

The terms "alkane" and "paraffinic hydrocarbon" mean substantially-saturated compounds containing hydrogen and carbon only, e.g., those containing ≤1% (molar basis) of unsaturated carbon atoms. As an example, the term alkane encompasses $C_2$ to $C_{20}$ linear, iso, and cyclo-alkanes. Aliphatic hydrocarbon means hydrocarbon that is substantially free of hydrocarbon compounds having carbon atoms arranged in one or more rings.

The term "unsaturate" and "unsaturated hydrocarbon" refer to one or more $C_{2+}$ hydrocarbon compounds which contain at least one carbon atom directly bound to another carbon atom by a double or triple bond. The term "olefin" refers to one or more unsaturated hydrocarbon compound containing at least one carbon atom directly bound to another carbon atom by a double bond. In other words, an olefin is a compound which contains at least one pair of carbon atoms, where the first and second carbon atoms of the pair are directly linked by a double bond. The term "aromatics" and "aromatic hydrocarbon" mean hydrocarbon compounds containing at least one aromatic ring. Non-aromatic hydrocarbon is hydrocarbon comprising ≤1 wt. % of carbon atoms included in aromatic rings.

The term "Periodic Table" means the Periodic Chart of the Elements, as it appears on the inside cover of The Merck Index, Twelfth Edition, Merck & Co., Inc., 1996.

"Dehydrocyclization" means removing hydrogen from and cyclizing a non-cyclic hydrocarbon to produce aromatic hydrocarbon and typically (i) cyclo-paraffin and/or (ii) cyclo-olefin. Dehydrocyclization can be carried out in one step which includes both dehydrogenation and cyclization. Dehydrocyclization can also be carried out in two steps, e.g., dehydrogenation followed by cyclization of the dehydrogenated intermediate; or in three or more steps, e.g., normal paraffin dehydrogenation, cyclization of the olefinic intermediate, and additional dehydrogenation (aromatization) of the cyclo-olefin intermediate. The dehydrocyclization (including any dehydrogenation carried out in connection with dehydrocyclization) is "non-oxidative" meaning that the reaction is carried out with little if any oxidative coupling of feed hydrocarbon, intermediate hydrocarbon (if any), or dehydrocyclization product.

The terms "reaction zone" or "reactor zone" mean a location within a reactor, e.g., a specific volume within a reactor, for carrying out a specified reaction. A reactor or reaction stage can encompass one or more reaction zones. More than one reaction can be carried out in a reactor, reactor stage, or reaction zone. For example, a reaction stage can include a first zone for carrying out first and second reactions and a second zone for carrying out a third reaction, where the first reaction (e.g., dehydrocyclization) can be the same as or different from the second reaction, and the third reaction (e.g., $CO_2$ methanation) can be the same as or different from the second reaction. When the reaction zone contains catalyst, the reaction can feature an average residence time of the catalyst in the reaction zone under the reaction conditions. The catalyst can, e.g., reside in a fixed catalyst bed located in a zone of a reactor. In these configurations, the zone is a reaction zone when the catalyst is exposed to the desired feed under the desired reaction conditions (reaction mode). The zone is a regeneration zone when the catalyst is exposed to a regenerating medium (e.g., air) under catalyst regeneration conditions (regeneration mode). These configurations can be operated continuously by switching between reaction mode and regeneration mode cyclically (e.g., in sequence). In these configurations, the average residence time is the average time the catalyst in the zone is exposed to the desired feed and the desired reaction conditions, e.g., the average time between the start of reaction mode operation and the start of regeneration mode operation, such as the average duration of reaction mode operation. For typical catalyst beds, the average residence time is the time period from (i) the time at which a bed of fresh or freshly regenerated catalyst is first exposed to the specified catalytic dehydrocyclization conditions to (ii) the time at which the catalyst bed is removed from dehydrocyclization service, e.g., for replacement and/or regeneration. A fixed catalyst bed can be removed from dehydrocyclization service by, e.g., discontinuing feed flow and/or exposing the bed to conditions other than the specified dehydrocyclization conditions. In cyclic operation over repeated reaction and regeneration modes, the time period is numerically averaged over the number of cycles. In other configurations, a reaction zone and regeneration zone operate at the same time, e.g., in separate vessels. For example, a first bed of catalyst particles can be located in the reaction zone, with a second bed of catalyst particles located in the regeneration zone. Catalyst particles withdrawn from the reaction zone bed can be transferred to the regeneration zone's bed for regeneration. In typically fluidized bed operation, the catalyst is removed from dehydrocyclization service by gradually withdrawing catalyst particles from the bed at a mass flow rate $MFR_1$ until 100% of the bed's mass ("M") is removed. In these aspects, the average time period is the average amount of time needed to remove 100% of the bed's catalyst particles, e.g., $[M/MFR_1]$.

The term "selectivity" refers to the production (on a weight basis) of a specified compound in a catalytic reaction. As an example, the phrase "a light hydrocarbon conversion reaction has 100% selectivity for aromatic hydrocarbon" means that 100% of the light hydrocarbon (weight basis) that is converted in the reaction is converted to aromatic hydrocarbon. When used in connection with a specified reactant, the term "conversion" means the amount of the reactant (weight basis) consumed in the reaction. For example, when the specified reactant is $C_4$ paraffinic hydrocarbon, 100% conversion means 100% of the $C_4$ paraffinic hydrocarbon is consumed in the reaction. Yield (weight basis) is conversion times selectivity.

Certain non-aromatic $C_{2+}$ hydrocarbon feeds useful for the dehydrocyclization will now be described in more detail. The invention is not limited to these feeds, and this description is not meant to foreclose the use of other feeds within the broader scope of the invention.

Representative Feeds

The feed typically comprises one or more $C_2$ to $C_9$ non-aromatic hydrocarbon compounds, e.g., one or more light hydrocarbon (i.e., $C_2$ to $C_5$) compounds, such as one or more paraffinic light hydrocarbon compounds. For example, the feed can comprise ≥1 wt. % based on the weight of the feed of one or more of (i) paraffinic $C_2$ to $C_9$ hydrocarbon, (ii) aliphatic $C_2$ to $C_9$ hydrocarbon, (iii) aliphatic paraffinic $C_2$ to $C_9$ hydrocarbon, (iv) paraffinic light hydrocarbon, (v) aliphatic light hydrocarbon, and (vi) aliphatic paraffinic light hydrocarbon; such as ≥10 wt. %, or ≥25 wt. %, or ≥50 wt. %, or ≥75 wt. %, or ≥90 wt. %, or ≥95 wt. %. Optionally, the feed further comprises diluent. Diluent present in the feed's source (e.g., methane and/or $CO_2$ present in natural gas) and diluent added to the feed are within the scope of the invention. Diluent, when present, is typically included in the feed in an amount ≤60 wt. % based on the weight of the feed, e.g., ≤50 wt. %, such as ≤40 wt. %, or ≤30 wt. %, or ≤20 wt. %, or ≤10 wt. %. A feed constituent is diluent when it is substantially non-reactive under the specified reaction conditions in the presence of the specified dehydrocyclization catalyst, e.g., methane, molecular nitrogen, and inert atomic gasses such as argon.

The feed typically contains $C_3$ and/or $C_4$ hydrocarbon e.g., (i) ≥20 wt. % propane, such as ≥40 wt. %, or ≥60 wt. %, and/or (ii) ≥20 wt. % butanes, such as ≥40 wt. %, or ≥60 wt. %. Although the feed can contain $C_{5+}$ hydrocarbon, the amount of $C_{5+}$ hydrocarbon when present is typically small, e.g., ≤20 wt. %, such as ≤10 wt. %, or ≤01 wt. %. Typically, the feed contains ≤10 wt. % of $C_{6|}$ saturated hydrocarbon, e.g., ≤5 wt. %.

The feed can contain methane, e.g., ≥1 wt. % methane, such as ≥10 wt. %, or ≥20 wt. %, or ≥60 wt. %. Even though methane is a diluent, i.e., it typically does not react to produce aromatic hydrocarbon or catalyst coke in the presence of the specified dehydrocyclization catalyst under the specified reaction conditions, its presence is beneficial. It is believed that this benefit results at least in part from a decrease in the partial pressure of the feed's $C_2$-$C_9$ hydrocarbon that is achieved when the feed further comprises methane. Decreasing the partial pressure of the feed's $C_2$-$C_9$ hydrocarbon, particularly the partial pressure of the feed's $C_2$-$C_5$ hydrocarbon, has been found to lessen the amount of catalyst coke formed under the specified dehydrocyclization process conditions. Typically, the feed comprises a total of ≤10 wt. % of impurities such as CO, $CO_2$, $H_2S$, and total mercaptan; e.g., ≤1 wt. %, or ≤0.1 wt. %. Optionally, the feed comprises molecular hydrogen, e.g., ≥1 wt. % molecular hydrogen based on the weight of the feed, such as ≥5 wt. %.

Optionally, the feed contains unsaturated $C_{2+}$ hydrocarbon, such as $C_2$-$C_5$ unsaturated hydrocarbon. When present, the amount of $C_{2+}$ unsaturated hydrocarbon is typically ≤20 wt. %, e.g., ≤10 wt. %, such as ≤1 wt. %, or ≤0.1 wt. %, or in the range of from 0.1 wt. % to 10 wt. %. The feed can be substantially-free of non-aliphatic hydrocarbon. More particularly, the feed can be substantially-free of aromatic hydrocarbon, where substantially-free in this context means ≤1 wt. % based on the weight of the feed, such as ≤0.1 wt. %, or ≤0.01 wt. %, or ≤0.001 wt. %. One representative feed comprises <1 wt. % ethane; ≤1 wt. % of aromatic hydrocarbon; and ≥1 wt. % of $C_{3+}$ paraffinic hydrocarbon, e.g., ≥10 wt. % of a mixture of $C_3$ and $C_4$, such as ≥50 wt. %, or ≥75 wt. %, or in the range of 80 wt. % to 99 wt. %. Another representative feed comprises (i) 10 wt. % to 40 wt. % ethane and ≤1 wt. % of aromatic hydrocarbon; with the feed further comprising (ii) 1 wt. % to 40 wt. % methane, (iii) 20 wt. % to 50 wt. % propane, and (iv) 20 wt. % to 50 wt. % butanes.

The feed's light hydrocarbon can be obtained from one or more sources of hydrocarbon, e.g., from natural hydrocarbon sources including those associated with producing petroleum, or from one or more synthetic hydrocarbons sources such as catalytic and/or non-catalytic reactions. Examples of such reactions include catalytic cracking, catalytic reforming, coking, steam cracking, etc. Synthetic hydrocarbon sources include those in which hydrocarbon within a geological formation has been purposefully subjected to one or more chemical transformations. The feed can include recycle components, e.g., a portion of a product recovered from the dehydrocyclization. Such recycle, when used, can include, e.g., methane, molecular hydrogen, and $C_{2+}$ hydrocarbon, typically $C_2$ to $C_5$ hydrocarbon.

In certain aspects, the source of light hydrocarbon includes natural gas, e.g., raw natural gas ("raw gas"). Natural gas is (i) a mixture comprising hydrocarbon, (ii) primarily in the vapor phase at a temperature of 15° C. and a pressure of 1.013 bar (absolute), and (iii) withdrawn from a geologic formation. Natural gas can be obtained, e.g., from one or more of petroleum deposits, coal deposits, and shale deposits. The natural gas can be one that is obtained by conventional production methods, but the invention is not limited thereto. Raw natural gas is a natural gas obtained from a geologic formation without intervening processing, except for (i) treatments to remove impurities such as water and/or any other liquids, mercaptans, hydrogen sulfide, carbon dioxide; and (ii) vapor-liquid separation, e.g., for adjusting the relative amounts of hydrocarbon compounds (particularly the relative amounts of $C_{4+}$ hydrocarbon compounds) in the natural gas; but not including (iii) fractionation with reflux. Conventional methods can be used for removing impurities and/or adjusting the relative amount of hydrocarbon compounds present in the feed, but the invention is not limited thereto. For example, certain components in the natural gas can be liquefied by exposing the natural gas to a temperature in the range of −57° C. to 15° C., e.g., −46° C. to 5° C., such as −35° C. to −5° C. At least a portion of the liquid phase can be separated in one or more vapor-liquid separators, e.g., one or more flash drums. One suitable raw natural gas comprises 3 mole % to 70 mole % methane, 10 mole % to 50 mole % ethane, 10 mole % to 40 mole % propane, and 5 mole % to 40 mole % butanes and 1 mole % to 10 mole % of total $C_5$ to $C_9$ hydrocarbon. In certain aspects, ≥50 wt. % of the feed comprises natural gas, such as raw natural gas, e.g., ≥75 wt. %, or ≥90 wt. %, or ≥95 wt. %.

Any form of raw gas can be used as a source material, although the raw gas is typically one or more of (i) gas obtained from a natural gas well ("Gas Well", Non-associated", or "Dry" gas), (ii) natural gas obtained from a condensate well ("Condensate Well Gas"), and (iii) casing head gas ("Wet" or "Associated" gas). Table 1 includes typical raw gas compositional ranges (mole %) and, parenthetically, typical average composition (mole %) of certain raw gasses.

TABLE 1

| Component | Associated Gas | Dry Gas | Condensate Well Gas |
|---|---|---|---|
| $CO_2$ | 0-50 (0.63) | 0-25 (0) | 0-25 (0) |
| $N_2$ | 0-50 (3.73) | 0-25 (1.25) | 0-25 (0.53) |
| $H_2S$ | 0-5 (0.57) | 0-5 (0) | 0-5 (0) |
| $CH_4$ | 0-80 (64.48) | 0-97 (91.01) | 0-98 (94.87) |
| $C_2H_6$ | 5-20 (11.98) | 2-10 (4.88) | 1-5 (2.89) |
| $C_3H_8$ | 2-10 (8.75) | 0.5-5 (1.69) | 0.1-5 (0.92) |
| i-butane | 0.1-5 (0.93) | 0.05-1 (0.14) | 0.1-5 (0.31) |
| n-butane | 1-5 (2.91) | 0.05-2 (0.52) | 0.05-2 (0.22) |
| i-pentane | 0.05-2 (0.54) | 0.01-1 (0.09) | 0.1-1 (0.09) |

In certain aspects, the feed comprises ≥75 wt. % Associated Gas, based on the weight of the feed, e.g., ≥90 wt. %, or ≥95 wt. %. Associated Gas is typically found with petroleum deposits, e.g., dissolved in the oil or as a free "gas cap" above the oil in a reservoir. In conventional petroleum production, the lack of effective natural transportation facilities, e.g., the lack of natural gas liquefaction and/or pipeline facilities, can result in Associated Gas being stranded at or near the reservoir. This in turn can lead to a need for undesirable natural gas flaring. Moreover, even in locations where pipeline facilities are available, Associated Gas may be excluded from the pipeline because it typically exceeds one or more pipeline specifications, e.g., ≤12 wt. % ethane, ≤5 wt. % propane, ≤2 wt. % butanes, a Wobbe Index of from 49.01 MJ/sm$^3$ to 52.22 MJ/sm$^3$), and a heating value of from 36.07 MJ/sm$^3$ to 41.40 MJ/sm$^3$).

Since methane is not detrimental to the process, and is in at least some aspects beneficial, the invention obviates the need for costly and inefficient cryogenic methane separation facilities, such as one or more conventional cold boxes. Typically, obtaining the feed from the source material (e.g., natural gas, such as raw gas) does not include (i) exposing the feed, source material, or any intermediate thereof to a temperature ≤−37° C., e.g., ≤−46° C., such as ≤−60° C. Certain aspects of the invention do not include cryogenic processing, e.g., cryogenic methane separation is not used.

The invention is advantageous in remote or under-developed locations, where (i) the lack of cryogenic methane separation facilities limits the utility of conventional natural gas aromatization processes, (ii) the lack of a pipeline or natural gas production infrastructure, may result in significant quantities of light hydrocarbon being flared or burned as fuel, and (iii) Associated Gas remains stranded at a remote location for lack of pipeline facilities or a failure to meet one or more specifications of an available pipeline. Small scale plants using the present process would allow effective recovery of these light hydrocarbon resources as liquid hydrocarbons. The invention is particularly advantageous for upgrading relatively refractory paraffinic hydrocarbon such as ethane. Accordingly, the feed can comprise ethane in an amount ≥1 wt. %, e.g., ≥5 wt. %, such as ≥10 wt. %. Suitable feeds include those containing a major amount of ethane, e.g., >50 wt. % ethane, such as ≥75 wt. %, or ≥90 wt. %, or ≥95 wt. %. For example, the feed can comprise an amount of ethane in the range of from 1 wt. % to 99 wt. %, such as 5 wt. % to 95 wt. %, or 10 wt. % to 90 wt. %. One representative feed comprises (i) ≥10 wt. % ethane, or ≥50 wt. %, or ≥90 wt. %, such as in the range of from 10 wt. % to 99.5 wt. % ethane, with ≥95 wt. % of the balance of the feed comprising one or more of methane, propane, and butanes.

The specified feed is exposed to the dehydrocyclization catalyst under dehydrocyclization conditions, the dehydrocyclization catalyst having an average residence time in the reaction zone under the dehydrocyclization conditions of ≤90 seconds, to convert at least a portion of the feed's $C_{2+}$ non-aromatic hydrocarbon to aromatic hydrocarbon. Certain aspects of the dehydrocyclization catalyst will now be described in more detail. The invention is not limited to these aspects, and this description is not meant to foreclose other aspects of the dehydrocyclization catalyst within the broader scope of the invention.

Representative Catalysts

Typically, the dehydrocyclization catalyst includes ≥10 wt. % of the molecular sieve component and ≥0.005 wt. % of the dehydrogenation component, wherein the molecular sieve component has a Constraint Index in the range of from 1-12, and the dehydrogenation component comprises one or more elements selected from Groups 3 to 13 of the Periodic Table. When the molecular sieve component and dehydrogenation component together include less than 100 wt. % of the catalyst, ≥90 wt. % of the remainder of the catalyst can include a matrix component, such as ≥99 wt. % of the remainder.

The catalyst typically includes the molecular sieve component in an amount ≥20 wt. %, based on the weight of the catalyst, e.g., ≥25 wt. %, such as ≥50 wt. %, or in the range of from 30 wt. % to 99.9 wt. %. In certain aspects, the molecular sieve component includes aluminosilicate, e.g., ≥90 wt. % of at least one aluminosilicate. The aluminosilicate can be an un-substituted aluminosilicate, a substituted aluminosilicate, or a combination thereof. For example, the aluminosilicate can be in a form where at least a portion of its original metal has been replaced, e.g., by ion exchange, with other suitable metal (typically metal cation) of Groups 1-13 of the Periodic Table. Typically, the aluminosilicate includes zeolite aluminosilicate, e.g., ≥90 wt. % of at least one zeolite based on the weight of the aluminosilicate. The term zeolite includes those in which at least part of the aluminum is replaced by a different trivalent metal, such as gallium or indium.

The molecular sieve component typically includes ≥90 wt. % of one or more of the specified molecular sieves, e.g., ≥95 wt. %. In certain aspects, the molecular sieve component includes at least one zeolite molecular sieve, e.g., ≥90 wt. % zeolite, such as ≥95 wt. %, based on the weight of the molecular sieve component. The molecular sieve component can consist essentially of zeolite, consist of zeolite, or can include zeolite in combination with other (e.g., non-zeolitic) molecular sieve. The zeolite can be in hydrogen form, e.g., zeolite synthesized in the alkali metal form and then converted to the hydrogen form. Typically the zeolite has a medium pore size and a Constraint Index of 2-12 (as defined in U.S. Pat. No. 4,016,218). Optionally, the zeolite has at least one set of pores of substantially uniform size extending through the molecular sieve, wherein geometric mean of the cross-sectional dimensions of each of the sets of pores is >5 Å, or >5.3 Å, e.g., ≥5.4 Å such as ≥5.5 Å, or in the range of 5 Å to 7 Å, or 5.4 Å to 7 Å. Examples of suitable zeolites include ZSM-5 (including H-ZSM-5), ZSM-11, ZSM-12, ZSM-22, ZSM-23, ZSM-35, and ZSM-48, including mixtures and intermediates thereof such as ZSM-5/ZSM-11 admixture. For example, the molecular sieve component can include ≥90 wt. % of (A) ZSM-5 and/or (B) ZSM-12, based on the weight of the molecular sieve component, e.g., ≥95 wt. % of H-ZSM-5. In certain aspects, the molecular sieve has a relatively small crystal size, e.g., small crystal ZSM-5, meaning ZSM-5 having a crystal size ≤0.05 micrometers (µm), such as in the range of 0.02 µm to 0.05 µm. Small crystal ZSM-5 and the method for determining molecular sieve crystal size are disclosed in U.S. Pat. No. 6,670,517, which is incorporated by reference herein in its entirety.

In other aspects, the molecular sieve component includes at least one molecular sieve of the MCM-22 family (including mixtures of MCM-22 family molecular sieve), e.g., MCM-22 alone or in combination with other molecular sieve such as one or more of the specified zeolites. The MCM-22 family includes those molecular sieves having an X-ray diffraction pattern including d-spacing maxima (in A) at 12.4±0.25, 6.9±0.15, 3.57±0.07 and 3.42±0.07. Examples of suitable MCM-22-family molecular sieve include PSH-3, SSZ-25, ITQ-1, MCM-36, MCM-49, MCM-56, UZM-8, ERB-1, and ITQ-2.

When the molecular sieve component includes at least one aluminosilicate, the aluminosilicate's silica:alumina ratio (substantially the same as the aluminosilicate's $Si:Al_2$ atomic ratio) is typically ≥2, e.g., in the range of from 5 to 100. The silica:alumina ratio is meant to represent the $Si:Al_2$ atomic ratio in the rigid anionic framework of the crystalline aluminosilicate. Alternatively or in addition, the catalyst can be made more resistant to deactivation (and increase aromatic hydrocarbon yield) by including phosphorous with the molecular sieve component. When used, the amount of phosphorous is typically ≥1 wt. % based on the weight of the molecular sieve component. For example, when the molecular sieve component includes aluminosilicate, the phosphorous:aluminum atomic ratio can be in the range of from 0.01 to 1. Zeolite having a higher silica:alumina ratio can be utilized when a lower catalyst acidity is desired, e.g., in the range of from 44 to 100, such as from 50 to 80, or 55 to 75. When the catalyst includes aluminosilicate which includes phosphorous, the phosphorous:aluminum atomic ratio is typically in the range of from 0.01 to 0.5. For example, the catalyst can contain ≥10 wt. % of phosphorous-modified alumina, such as ≥15 wt. %, or in the range of from 10 wt. % to 20 wt. %.

In addition to the molecular sieve component, the catalyst includes ≥0.005 wt. %, based on the weight of the catalyst, of a dehydrogenation component, e.g., at least one dehydrogenation metal. The dehydrogenation component can include one or more neutral metals selected from Groups 3 to 13 of the Periodic Table, such as one or more of Ga, In, Zn, Cu, Re, Mo, W, La, Fe, Ag, Pt, and Pd, and/or one or more oxides, sulfides and/or carbides of these metals. For example, the dehydrogenation component can be Ga, Zn, or a combination thereof, optionally supported on a catalyst including ZSM-5 as the molecular sieve component.

Typically, the dehydrogenation component includes ≥90 wt. % of the one or more of the specified dehydrogenation metals and/or oxide thereof, e.g., ≥95 wt. %, or ≥99 wt. %. For example, the dehydrogenation component can include ≥90 wt. % of (A) Ga and/or (B) Zn, including oxides thereof. Typically, the catalyst includes ≥0.01 wt. % of the dehydrogenation component, based on the weight of the catalyst, e.g., ≥0.1 wt. % of the dehydrogenation component, such as ≥0.5 wt. %, or ≥1 wt. %.

Those skilled in the art will appreciate that when the dehydrogenation component includes one or more metals of greater catalytic dehydrogenation activity, e.g., Pt, and/or Pd, a lesser amount of dehydrogenation component is needed, e.g., in the range of 0.005 wt. % to 0.1 wt. %, based on the weight of the catalyst, such as 0.01 wt. % to 0.6 wt. %, or 0.01 wt. % to 0.05 wt. %. When the dehydrogenation component includes one or more metals of lesser dehydrogenation activity, e.g., one or more of Ga, In, Zn, Cu, Re, Mo, and W, a greater amount of dehydrogenation component is needed, e.g., in the range of 0.05 wt. % to 10 wt. %, based on the weight of the catalyst, such as 0.1 wt. % to 5 wt. %, or 0.5 wt. % to 2 wt. %.

The dehydrogenation component can be provided on, in, or proximate to the catalyst in any manner, for example by conventional methods such as impregnation or ion exchange. At least part of the dehydrogenation metal may also be present in the crystalline framework of the molecular sieve. For one representative catalyst, (i) the dehydrogenation component includes ≥95 wt. % of (A) Ga and/or (B) Zn, and (ii) the first molecular sieve component includes ≥95 wt. % of H-ZSM-5.

In certain aspects, the dehydrogenation component includes ≥99 wt. % of one or more of Ga, Zn, and In, and the molecular sieve component includes ≥99 wt. % of ZSM-5-type zeolite that has been impregnated with the dehydrogenation metal component and/or ion exchanged with the dehydrogenation metal component. For example, the catalyst can include Ga-impregnated and/or In-impregnated H-ZSM-5, Ga-exchanged and/or In-exchanged H-ZSM-5, H-gallosilicate of ZSM-5 type structure and H-galloaluminosilicate of ZSM-5 type structure. Optionally, the catalyst includes (i) tetrahedral aluminum and/or gallium, which is present in the zeolite framework or lattice, and/or (ii) octahedral gallium or indium, which is not present in the zeolite framework but present in the zeolite channels in close vicinity to the zeolitic protonic acid sites. While not wishing to be bound by any theory or model, the tetrahedral or framework Al and/or Ga is believed to contribute to acid function of the catalyst and octahedral or non-framework Ga and/or In is believed to contribute to the dehydrogenation function of the catalyst. Although typically the zeolite is impregnated or ion-exchanged with the dehydrogenation metal, other forms of zeolite can be used, such as H-galloaluminosilicate of ZSM-5 type structure having framework (tetrahedral) Si/Al and Si/Ga atomic ratios of about 10:1 to 100:1 and 15:1 to 150:1, respectively, and non-framework (octahedral) Ga of about 0.5 wt. % to 0 wt. %.

Besides the molecular sieve component and dehydrogenation component, the catalyst can further include an optional matrix component, e.g., one or more inorganic binders. The amount of matrix component is not critical. When present, the amount of matrix component is typically in the range of 0.01 times the weight of the molecular sieve component to about 0.9 times the weight of the molecular sieve component, e.g., in the range of 0.02 to 0.8. The matrix component can include active materials, such as synthetic or naturally occurring zeolites. Alternatively, or in addition, the matrix component can include clays and/or oxides such as alumina, silica, silica-alumina, zirconia, titania, magnesia or mixtures of these and other oxides. The matrix component can include naturally occurring materials and/or materials in the form of gelatinous precipitates or gels including mixtures of silica and metal oxides. Clays may also be included with the oxide type binders to modify the mechanical properties of the catalyst or to assist in its manufacture.

Alternatively or in addition, the matrix component can include one or more substantially inactive materials. Inactive materials suitably serve as diluents to control the amount of conversion so that products may be obtained economically and orderly without employing other means for controlling the rate of reaction. Alternatively or in addition to any phosphorous added to or impregnated into the molecular sieve component, the matrix component can optionally include phosphorous, e.g., to lessen catalyst acidity. Those skilled in the art will appreciate that lessening catalyst acidity decreases the amount of catalyst coke produced during the catalytic conversion of the feed's light hydrocarbon to aromatic hydrocarbon. Suitable phosphorous-containing matrices are disclosed in U.S. Pat. No. 5,026,937, which is incorporated by reference herein in its entirety. The matrix component is optional. In certain aspects, the catalyst is substantially-free of matrix, e.g., contains ≤1 wt. % of matrix, such as ≤0.1 wt. %. In particular, the catalyst can be substantially free of binder, e.g., contains ≤1 wt. % of binder, such as ≤0.1 wt. %. For example, the catalyst's molecular sieve component can includes ≥95 wt. % substantially binder-free bound molecular sieve, e.g., ≥95 wt. % of substantially binder-free ZSM-5, and in particular small crystal H-ZSM-5.

The dehydrocyclization catalyst can be subjected to one or more treatments, e.g., a selectivation treatment to increase selectivity for producing desired aromatic hydrocarbon compounds such as para-xylene. For example, the selectivation can be carried out before introduction of the catalyst into the reactor and/or in-situ in the reactor, e.g., by contacting the catalyst with a selectivating agent, such as at least one organosilicon in a liquid carrier and subsequently calcining the catalyst at a temperature of 350° C. to 550° C. This selectivation procedure can be repeated two or more times and alters the diffusion characteristics of the catalyst such that the formation of para-xylene over other xylene isomers is favored. Such a selectivation process is described in detail in U.S. Pat. Nos. 5,633,417 and 5,675,047.

In particular aspects, e.g., those where it is desired to convert <50 wt. % of any feed ethane, the dehydrocyclization catalyst (Catalyst A) has a molecular sieve component which includes ≥90 wt. % of an aluminosilicate in hydrogen form, the aluminosilicate having a constraint index in the range of from 2-12 (e.g., phosphorous-modified H-ZSM-5) and a silica to alumina ratio in the range of from 50 to 80. For example, the molecular sieve component can include ≥95 wt. % of substantially binder-free, small crystal H-ZSM-5. For Catalyst A, the dehydrogenation component can include ≥90 wt. % of at least one oxide of Ga. The matrix component, when used, can include ≥75 wt. % of alumina, silica, and combinations thereof. Catalyst A optionally includes ≥1 wt. % phosphorus, e.g., in the form of phosphorous-modified H-ZSM-5 and/or by including phosphorous in the matrix component.

In other aspects, e.g., those where it is desired to convert ≥50 wt. % of the feed's ethane, the dehydrocyclization catalyst (Catalyst B) typically has greater acidity than that of Catalyst A. For Catalyst B, the molecular sieve component can include ≥90 wt. % of an aluminosilicate in hydrogen form, the aluminosilicate having a constraint index in the range of from 2-12 (e.g., small crystal, H-ZSM-5). Typically, the dehydrocyclization catalyst of Catalyst B has (i) a silica:alumina ratio in the range of from 3 to 60, e.g., from 10 to 40, such as from 15 to 35, and (ii) <0.01 wt. % phosphorus. It is also typical for Catalyst B's dehydrogenation component to include ≥90 wt. % of (i) at least one oxide of Zn and/or (ii) at least one oxide of Ga, such as ≥95 wt. % of at least one oxide of Zn. The matrix component when used includes ≥90 wt. % of alumina, silica, and combinations thereof.

The specified dehydrocyclization catalysts can have any convenient form that is useful in the specified dehydrocyclization reaction. For example, the catalyst can have the form of a particulate, e.g., a plurality of catalyst particles having an average size ≤250 μm, e.g., in the range of 20 μm to 200 μm, and an average density in the range of from 0.6 g/cm$^3$ to 2 g/cm$^3$, e.g., in the range of from 0.9 g/cm$^3$ to 1.6 g/cm$^3$. Typically, the catalyst has a surface area, as measured by nitrogen physisorption, in the range of from 100 m$^2$/g to 600 m$^2$/g, e.g., in the range of from 200 m$^2$/g to 500 m$^2$/g. The catalyst can be located in one or more bed configurations, e.g., conventional bed configurations such as fixed bed, moving bed, ebullating bed, fluidized bed, etc. Any convenient reactor configuration can be used that is suitable for contacting the specified dehydrocyclization catalyst with the specified feed under the specified dehydrocyclization conditions for the specified average residence time in the reaction zone under the dehydrocyclization conditions. Conventional reactors are suitable, e.g., tubular reactors, including reverse-flow regenerative reactors, fluid-bed reactors, riser reactors, fixed bed reactors, etc. Any convenient method for controlling the average residence time in the reaction zone of the specified dehydrocyclization catalyst under the specified dehydrocyclization conditions can be used, including conventional methods for doing so, e.g., adding and removing catalyst from a fluidized bed via catalyst inlet and outlet conduits, conveying the catalyst through a riser reactor, operating flow control valves to regulate the flow of feed and regenerating fluid through a tube reactor containing the dehydrocyclization catalyst, etc.

Representative Dehydrocyclization Reactions

The dehydrocyclization reaction can be carried out by exposing the feed to one or more beds containing a catalytically effective amount of a catalyst selected from among the specified dehydrocyclization catalysts. The reaction is carried out under conditions effective for catalytic dehydrocyclization. The catalyst's average residence time in the reaction zone is typically ≤90 seconds. Representative dehydrocyclization conditions include a temperature in range of from 400° C. to 800° C., e.g., 600° C. to 800° C.; a pressure ≥10 psia (68.9 kPa), e.g., 0 psig (101 kPa) to 300 psig (2170 kPa); and a space velocity (GHSV)≥1100 hr$^{-1}$, e.g., in the range of from 1500 hr$^{-1}$ to 40,000 hr$^{-1}$; the dehydrocyclization catalyst having an average residence time in the reaction zone under the dehydrocyclization conditions of ≤90 seconds, e.g., in the range of from 0.01 seconds to 30 seconds. Those skilled in the art will appreciate that the specified temperature represents average temperatures across the catalyst bed. Average temperature is calculated by adding the bed's inlet temperature to the bed's outlet temperature, and then dividing the sum by 2. The specified pressure is not an average pressure. Instead, the specified pressure corresponds to that subsisting at the bed's inlet.

Typical process conditions include a temperature in range of from 630° C. to 750° C., e.g., 600° C. to 700° C.; a pressure in the range of from 20 psia (137.9 kPa) to 300 psig (2170 kPa), e.g., from 30 psia (207 kPa) to 80 psia (522 kPa); a space velocity (GHSV) in the range of from 2000 hr$^{-1}$ to 20,000 hr$^{-1}$, e.g., 2500 hr$^{-1}$ to 15,000 hr$^{-1}$. Typically, the dehydrocyclization catalyst has an average residence time in the reaction zone under the dehydrocyclization conditions of ≤60 seconds, e.g., ≤30 seconds, such as ≤10 seconds, or ≤1 second, or ≤0.1 second, in the range of from 0.001 second to 60 seconds, or 0.01 seconds to 30 seconds. For example, the catalyst can have an average residence time in the reaction zone under the dehydrocyclization conditions in the range of from 0.01 second to 10 seconds, e.g., 0.1 second to 10 seconds, such as 0.1 seconds to 1 second.

In comparison with conventional processes, the reaction is capable of increased conversion of $C_{2+}$ hydrocarbon without a significant decrease in the selectivity for aromatic hydrocarbon, and without excessive selectivity for light hydrocarbon compounds such as methane. For example, aromatic hydrocarbon selectivity is typically ≥30 wt. %, e.g., ≥40 wt. %, such as ≥50 wt. %, or ≥60 wt. %. Methane selectivity is typically ≤40 wt. %, e.g., ≤30 wt. %, such as ≤20 wt. %. $C_{2+}$ paraffin selectivity is typically ≤5 wt. %, e.g., ≤1 wt. %. $C_{2+}$ olefin selectivity is typically ≤20 wt. %, e.g., ≤10 wt. %. Advantageously, the process exhibits high $C_{2+}$ conversion with low selectivity for methane over a wide range of conversion values. For example, the reaction can achieve (A) a $C_{2+}$ hydrocarbon conversion of X wt. % and (B) a methane selectivity of Y wt. %, wherein when (A) X>60, then Y≤40, (B) X is in the range of 50 to 60 then Y≤20, and (C) X<50 then Y≤15. For example, the process can have an aromatic hydrocarbon selectivity ≥40 wt. % and a methane selectivity ≤40 wt. %. Very large $C_{2+}$ hydrocarbon conversion can be achieved compared to conventional processes, and in particular very large ethane conversion can be achieved. For example, when the dehydrocyclization catalyst has an average residence time in the reaction zone under the dehydrocyclization conditions of ≤90 seconds, e.g., in the range of from 0.010 seconds to 30 seconds, $C_{2+}$ conversion (e.g., the $C_2$-$C_4$ paraffinic hydrocarbon conversion, and in particular ethane conversion) is typically ≥65 wt. %, e.g., ≥70 wt. %, such as ≥75 wt. %, or ≥80 wt. %, or in the range of 65 wt. % to 95 wt. %. Typically, the product has a total aromatic hydrocarbon content of ≥5 wt. %, based on the weight of the product, such as ≥10 wt. %, or in the range of 1 wt. % to 95 wt. %, or 10 wt. % to 75 wt. %. The process produces a desirable BTX product, typically having an increased yield of desirable xylene isomers and a decreased yield of less desirable $C_{11+}$ aromatic hydrocarbon in comparison with conventional processes. It can be desirable to alkylate at least a portion of the product to produce toluene and/or xylene, particularly when the product comprises benzene. Conventional alkylation processes (including successive alkylation processes) can be used, but the invention is not limited thereto. Examples of suitable alkylation processes are described in U.S. Pat. No. 6,642,426, and in U.S. Patent Application Publication No. 2015/0376088, these being incorporated by reference herein in their entireties.

Any convenient method can be employed for recovery of aromatic hydrocarbon from the product, including conventional methods such as boiling point separation, gravity separation, solvent extraction, etc. Non-aromatic $C_{2+}$ hydrocarbon is optionally recovered from the product, e.g., for recycle as a feed component. Methane and/or molecular hydrogen (e.g., tail gas) can also be recovered from the product, e.g., for storage, further processing, and/or use as a fuel.

In certain aspects, e.g., those where it is desired to convert <50 wt. % of any feed ethane, and particularly those using Catalyst A, the process conditions a temperature $T_1$ in the range of from 400° C. to 630° C., and a pressure $P_1$ that is sufficient for carrying out the dehydrocyclization. Typically, $T_1$ is in the range of from 450° C. to 605° C. Typically, $P_1$ is ≥20 psia (137.9 kPa) e.g., ≥35 psia (241.3 kPa), such as in the range of from 35 psia (241.3 kPa) to 300 psia (2070 kPa). For example, $P_1$ can be in the range of from 35 psia (241.3 kPa) to 300 psia (2070 kPa), such as 37 psia (255.1 kPa) to 80 psia (522 kPa), or 40 psia (275.8 kPa) to 80 psia (522 kPa), or 45 psia (310.2 kPa) to 80 psia (522 kPa). The average temperature across a bed of Catalyst A is typically ≤600° C., more typically in the range of from 20° C. to 200° C., e.g., in the range of from 50° C. to 150° C.

In other aspects, e.g., those where it is desired to convert ≥50 wt. % of the feed's ethane, and particularly those using Catalyst B, the process conditions can include a temperature $T_2$ in the range of from 450° C. to 700° C., and a pressure $P_2 \leq 35$ psia (241.3 kPa). Typically, $T_1 \leq 0.9 \cdot T_2$, e.g., $T_1 \leq 0.85 \cdot T_2$, such as $T_1 \leq 0.8 \cdot T_2$. The pressure $P_2$ is typically less than that of the first reactor, e.g., $P_2 \leq 0.95 \cdot P_1$, such as $P_2 \leq 0.90 \cdot P_1$, or $P_2 \leq 0.85 \cdot P_1$, or $P_2 \leq 0.8 \cdot P_1$. Typically, reaction conditions include $T_2$ in the range of from 500° C. to 675° C. and $P_2 \leq 34$ psia (234.4 kPa), e.g., ≤32 psia (220.6 kPa), such as ≤30 psia (207 kPa), or in the range of from 10 psia (68.9 kPa) to 35 psia (241.3 kPa) or from 12 psia (82.8 kPa) to 34 psia (234.4 kPa). As is the case for other aspects, $T_2$ represents an average temperature across the second catalyst bed, and $P_2$ corresponds to the pressure at the inlet of the second catalyst bed. Typically, the average temperature across a bed of Catalyst B is ≤700° C. Typically, the feed is not exposed to a temperature ≥700° C. at the inlet to the catalyst bed. The process can be operated in catalyst beds arranged in series, e.g., with the $C_{2i}$ non-aromatic hydrocarbon first contacting a bed of Catalyst A and the effluent from the first catalyst bed contacting a second bed containing Catalyst B. The first bed may be operated under conditions (e.g., $T_1$ and $P_1$) which convert primarily $C_{3+}$ non-aromatic hydrocarbon. The second bed may be operated under conditions (e.g., $T_2$ and $P_2$) favorable for ethane conversion. Although they are not required, these aspects are compatible with additional processing, e.g., one or more of heating the first bed's effluent upstream of the second bed, removing at least a portion of any aromatic hydrocarbon in the first bed's effluent upstream of the second bed, removing at least a portion of any molecular hydrogen in the first bed's effluent upstream of the second bed.

Regeneration of the Dehydrocyclization Catalyst

In certain aspects, the dehydrocyclization reaction is carried out in a plurality of reactors, each reactor containing at least one bed of an active material selected from among the specified dehydrocyclization catalysts. Each of the reactors can be substantially the same as the others, namely of substantially the same bed configuration and contain substantially the same amount of substantially the same catalyst. Typically, one or more of the reactors in reaction (dehydrocyclization) mode while the other(s) are operated in regeneration mode, and vice versa. Continuous or semi-continuous operation can be carried out in each stage, by alternating reactors in sequence in reaction and regeneration modes.

Regeneration of the dehydrocyclization catalyst includes removing at least a portion of any accumulated deposits from the catalyst, e.g., coke and/or coke precursors. Typically, the dehydrocyclization catalyst is regenerated at an inlet temperature ≤700° C. Exceeding this temperature during regeneration has been found to result in catalyst dealumination and/or loss of structure, leading to an undesirable loss of catalyst acidity. Catalyst regeneration for any of the specified catalysts is typically carried out using procedures which limit the maximum temperature to which the catalyst is exposed during regeneration to about 750° C., more typically to about 650° C. Conventional catalyst regeneration methods can be used, e.g., exposing the catalyst to at least one regeneration medium, e.g., an oxidant such as air or oxygen in air, for a time sufficient to remove at least a portion of the catalyst coke, but the invention is not limited thereto. Relatively uncommon regeneration media are within the scope of the invention, e.g., carbon dioxide, and/or molecular hydrogen. Typically, regeneration includes circulating a stream of regeneration medium containing a limited amount of oxygen, which limits the size of the exotherm where coke is burned off the catalyst. At the location where the regeneration medium enters the first (most upstream, with respect to the flow of regeneration medium) reactor, e.g., at the reactor's inlet, the regeneration medium is typically exposed to a temperature ≤350° C., e.g., ≤325° C., such as ≤300° C. If needed, the oxidant content of the regeneration medium can be decreased to lessen the risk of exceeding the maximum temperature. Alternatively, or in addition, regeneration can be carried out by passing a regeneration medium comprising a stream of molecular hydrogen in proximity to the catalyst, e.g., for catalyst coke methanation.

Fluidized Bed Operation

Although fixed catalyst beds, moving catalyst beds, fluidized catalyst beds, ebullating catalyst beds, combinations thereof, etc., are all within the scope of the invention, certain aspects which include carrying out dehydrocyclization in one or more fluidized beds will now be described in more detail. The invention is not limited to these aspects, and this description is not meant to foreclose the use of other catalyst bed configurations within the broader scope of the invention.

In fluidized bed aspects, the dehydrocyclization catalyst is typically in the form of a plurality of catalyst particles. The catalyst particles have an average catalyst particle residence time in the reaction zone of ≤90 seconds. The dehydrocyclization reaction is typically carried out in a reaction zone. Catalyst regeneration is carried out in a regeneration zone. During typical fluid bed operation, a portion of the dehydrocyclization catalyst is continuously transferred from the reaction zone to the regeneration zone, and regenerated dehydrocyclization catalyst is continuously transferred from the regeneration zone to the reaction zone. Besides being a convenient configuration for maintaining the specified average catalyst particle residence time in the reaction zone, using a fluidized catalyst bed can be operated at a lesser pressure drop than fixed bed configurations of approximately the same capacity. Improved temperature control within the dehydrocyclization reaction zone is also typically achieved over fixed bed configurations, which desirably allows the bed to be more isothermal. Any convenient form of fixed bed reactor can be used for carrying out the dehydrocyclization reaction, including conventional fluid bed reactors such as those described (for a different purpose) in U.S. Pat. No. 4,751,338.

Figure 2:
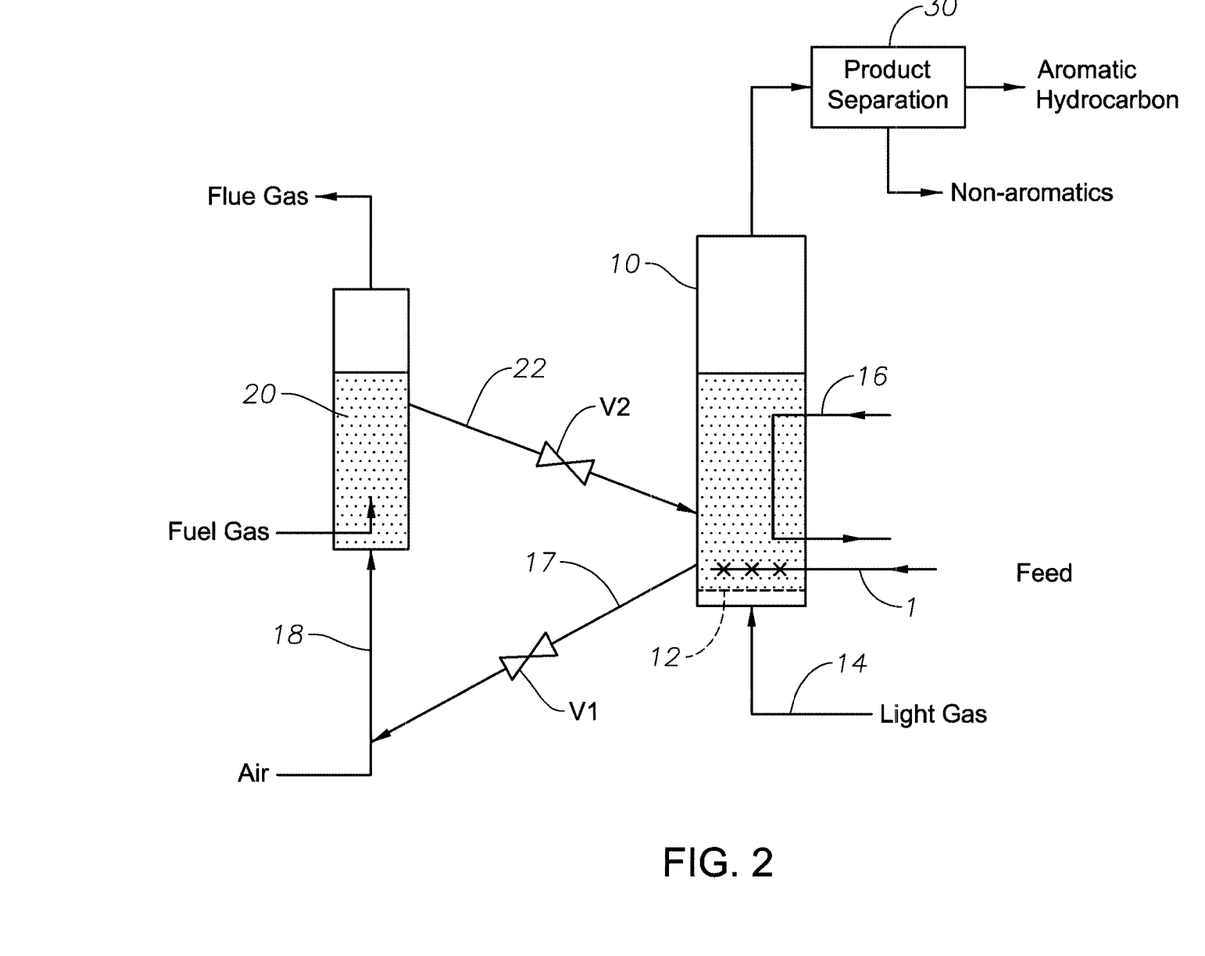
FIG. 2 is a schematic representation of certain aspects of the invention in which the dehydrocyclization reaction is carried out in a fluidized bed.

Referring FIG. 2, a $C_{2+}$ hydrocarbon feed is passed via feed conduit 1 for injection into reactor vessel 10 through one or more injectors proximate to a distributor grid 12. Additional feed or a lift gas can be passed via conduit 14 through grid 12 to provide additional lift, as might be needed when a major amount of the feed is in the vapor phase upstream of the injection. Fluidization is effected in the bottom portion of the bed by upwardly flowing feed and any optional lift gas. Process conditions in reactor 10 can be controlled within the specified dehydrocyclization ranges, e.g., by adjusting feed temperature, catalyst temperature, catalyst circulation rate, (e.g., via valves $V_1$ and/or $V_2$), or by an indirect transfer of heat to or from conduit 16, which can be used for circulating a heat transfer fluid.

The specified average catalyst particle residence time in the reaction zone is achieved by withdrawing catalyst from above grid 12 via conduit 7 provided with flow control valve $V_1$. The withdrawn catalyst is passed via air lift line 18 for catalyst regeneration in vessel 20 where combustible deposits (e.g., coke) are removed by oxidation with air or other regeneration gas. Should the combustion of these deposits provide insufficient heat to maintain the dehydrocyclization reaction in thermal balance, additional heat may be added via additional indirect heat transfer from the heat transfer fluid of conduit 16. Alternatively or in addition, further catalyst heating during regeneration can be used, e.g., conveying the catalyst in line 18 with heated vapor (such as heated nitrogen, heated oxygen, heated air, etc.) and/or combusting a flue gas or other fuel stream in the regenerator, provided the catalyst does not exceed the temperature at which catalyst dealumination and/or loss of structure would occur. Regenerated catalyst is returned to the reactor 10 via conduit 22 and valve $V_2$. To maintain the fluidized bed of reactor 10 in mass balance, the mass of the withdrawn catalyst is typically substantially the same as that of the replacement catalyst. In other words, $MFR_1$ can be substantially equal to the average mass flow rate of replacement catalyst added to the fluidized bed ($MFR_2$).

Although they are not shown, one or more cyclone particle separators can be used for removing entrained solids (e.g., catalyst fines) from the effluent of reactor 10, to produce the product. The product can be conducted to product separation stage 30, for separating from the product at least a portion of the product's aromatic hydrocarbon and optionally at least a portion of the product's non-aromatics. Non-aromatics can be recycled to the process, e.g., as feed and/or fuel components.

The dehydrocyclization catalyst in reactor 10 can have the form of a plurality of catalyst particles located in a turbulent bed, as indicated by the shaded region inside reactor 10. Typically, the bed has a density in the range of from 100 $kg/m^3$ to 500 $kg/m^3$ and a superficial fluid velocity in the range of 0.1 m/s to 10 m/s, such as 0.3 m/s to 2 m/s. Size distribution of the dehydrocyclization catalyst is selected so that the catalyst will mix well throughout the bed. Large particles, e.g., those having a particle size greater than 250 µm, are generally avoided. Typically, ≥50 wt. % of the catalyst is in a particle size range of from about 1 µm to 150 µm, e.g., ≥75 wt., or ≥90 wt. The dehydrocyclization typically has an average particle size in the range of about 20 µm to about 100 µm, e.g., 40 µm to 80 µm. It is also typical for the catalyst to have an average density in the range of from 0.6 $g/cm^3$ to 2 $g/cm^3$. The catalyst circulation rate is selected to achieve an average residence time for the dehydrocyclization catalyst in the bed of reactor 10 that is ≤90 seconds, e.g., ≤60 seconds, such as ≤30 seconds, or ≤10 seconds, or ≤1 second, or in the range of from 0.1 seconds to 10 seconds. For an appropriately-sized reactor vessel 10 having a bed of volume $V_B$ of fluidized dehydrocyclization catalyst, the circulation rate can be adjusted in the desired range using valves $V_1$ and $V_2$. Typically, fresh or freshly-regenerated catalyst is added to the process to replace catalyst and/or catalyst fines removed from the process, e.g., during product recovery. This is an aid in maintaining $V_B$ substantially constant. In certain aspects, the dehydrocyclization catalyst is removed from (and added to) the fluid bed of reactor 10 at a rate >0.11 $V_B$/second, e.g., ≥0.017 $V_B$/second, such as ≥0.033 $V_B$/second, or ≥0.1 $V_B$/second, or ≥1 $V_B$/second, or in the range of from 0.03 $V_B$/second to 100 $V_B$/second, or 0.1 $V_B$/second to 10 $V_B$/second. Those skilled in the art will appreciate that riser reactors such as those used for carrying out fluidized catalytic cracking reactions may be a more appropriate form of fluidized catalyst reactor than that of FIG. 2 when the catalyst particle residence time in the reaction zone is of relatively short duration, e.g., in the range of from 0.010 second to 0.1 second (equivalent to 10 $V_B$/second to 100 $V_B$/second). Typically, ≥90 wt. % of the replacement catalyst particles comprise regenerated catalyst particles. It is also typical for the freshly regenerated catalyst particles of conduit 22 to be at a greater temperature than the equilibrium dehydrocyclization catalyst in the fluid bed of reactor 10, but in other respects to have substantially the same physical, chemical, and compositional properties. The invention is not limited to aspects having one fluidized bed for carrying out the dehydrocyclization and one fluidized bed for carrying out the regeneration. Fluidized bed reactors systems having a plurality of fluidized beds for carrying out one or more of the specified dehydrocyclization reactions and/or one or more of the specified regenerations are within the scope of the invention, including those having a plurality of reactor and/or regenerator vessels. In particular, the dehydrocyclization is carried out in a staged fluidized bed reactor.

Example

A ZSM-5 molecular sieve, catalog number CBV3014E, is obtained Zeolyst International of Conshohocken, Pa. An impregnation solution is prepared by combining gallium nitrate and water. A catalyst precursor is prepared by (i) combining the impregnation solution with 40 grams of the ZSM-5 molecular sieve to produce a mixture and (ii) removing water from the mixture by heating the mixture to a temperature of 100° C. for two hours to remove water. The catalyst precursor is calcined by heating the precursor in air to a temperature 630° C. for six hours to produce a dehydrogenation catalyst comprising ZSM-5 and 1.5 wt. % gallium. The dehydrogenation catalyst is cooled to a temperature of 25° C. A fixed catalyst bed containing one gram of the cooled dehydrocyclization catalyst is located in an isothermal, plug-flow tube reactor. The reactor is heated to a temperature of 230° C., and a flow of ethane is established into the reactor at a GHSV of 3072 $hr^{-1}$. While maintaining a total pressure of two bar (absolute), the reactor is heated to a temperature of 630° C., and the reactor's gaseous effluent is sampled three times. The first sample is taken approximately one second after the catalyst first achieves a temperature of 630° C. The second sample is taken approximately 75 minutes after the catalyst first achieves a temperature of 630° C. The third sample is taken approximately 150 minutes after the catalyst first achieves a temperature of 630° C. Feed conversion is plotted on FIG. 1, as are the effluent's aromatic hydrocarbon content, olefin content, paraffin content, methane content and naphthalenes content (all wt. %, based on the weight of the effluent).

Figure 1:
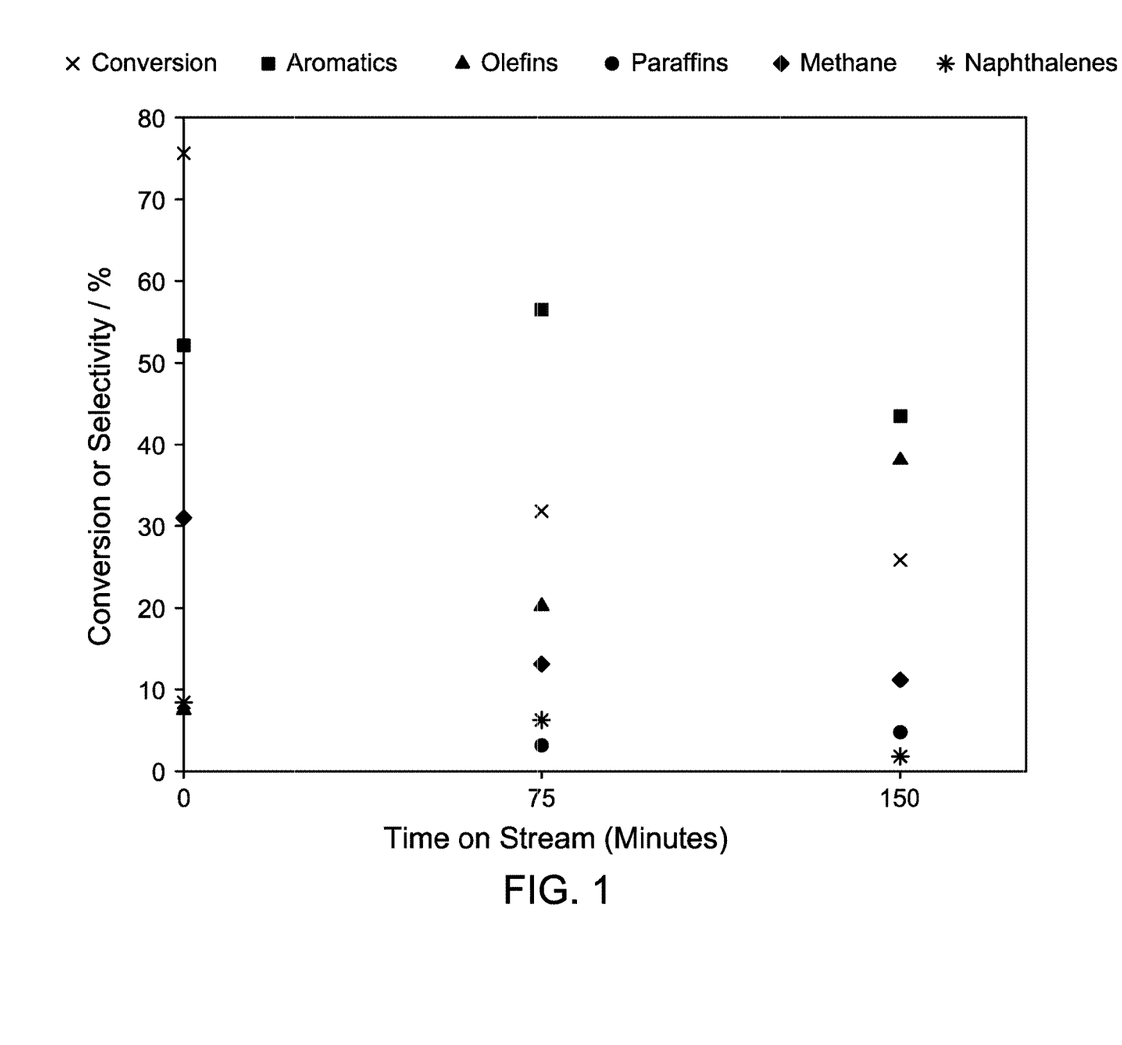
FIG. 1 is a graph illustrating an increase in ethane conversion that is achieved in Example 1 when the dehydrocyclization catalyst has average residence time in the reaction zone under the dehydrocyclization conditions ≤90 seconds.

Extrapolating from the conversions indicated at the second and third samplings, the conversion expected when the dehydrocyclization catalyst has an average residence time of about two minutes in the reaction zone under the dehydrocyclization conditions is expected to be approximately 40 wt. %, with an effluent aromatic hydrocarbon content of about 60 wt. %. These approximations are consistent with the results disclosed in Example 1 of U.S. Patent Application Publication No. 2009/0209794 A1. One skilled in the art who further extrapolates from these data to an average residence time of one second for the dehydrocyclization catalyst in the reaction zone under the dehydrocyclization conditions would expect little if any change from the values predicted for a time of two minutes. It is therefore very surprising that a dramatic deviation from the extrapolated conversion is observed when the dehydrocyclization catalyst has a residence time in the reaction zone under reaction conditions of about 90 seconds or less, as indicated by the data for the first sampling. The observed conversion of approximately 75 wt. % is nearly twice the value expected from the prior art or from an interpolation using data from samplings two and three. Although the first sampling indicates a methane yield that is greater than expected and an aromatics yield that is less than expected, these effects are more than overcome by the dramatic increase in ethane conversion, resulting in a significant increase in aromatic hydrocarbon recovery over the expected value.

All patents, test procedures, and other documents cited herein, including priority documents, are fully incorporated by reference to the extent such disclosure is not inconsistent and for all jurisdictions in which such incorporation is permitted. Although certain aspects are described herein with particularity, other aspects will be apparent to and can be readily practiced by those skilled in the art without departing from the spirit and scope of the invention. Accordingly, it is not intended that the scope of the claims appended hereto be limited to the examples and descriptions set forth herein but rather that the claims be construed as encompassing all the features of patentable novelty which reside herein, including all features which would be treated as equivalents thereof by those skilled in the art to which this disclosure pertains. When lower and upper limits are specified, ranges from any lower limit to any upper limit are expressly within the scope of the invention. The term "comprising" is synonymous with the term "including". When a composition, an element or a group of components is preceded with the transitional phrase "comprising", the same composition or group of components is within transitional phrases "consisting essentially of," "consisting of," "selected from the group of consisting of," or "is" preceding the recitation of the composition, component, or components, and vice versa.

The invention claimed is:

1. A process for producing aromatic hydrocarbon, comprising:
   (a) providing a feed comprising ≥1 wt. % of $C_{2+}$ non-aromatic hydrocarbon;
   (b) providing a catalyst having catalytic activity for dehydrocyclization of the $C_{2+}$ non-aromatic hydrocarbon, wherein the catalyst includes a molecular sieve component and a dehydrogenation component;
   (c) converting ≥70 wt. % of the feed's $C_{2+}$ non-aromatic hydrocarbon to produce a product comprising ≥1 wt. % of aromatic hydrocarbon, the conversion being carried out in a conversion zone in the presence of the catalyst under conversion conditions which include a temperature in the range of from 400° C. to 800° C., a pressure in the range of from 0 psig (101 kPa) to 300 psig (2170 kPa), wherein the catalyst has an average residence time in the conversion zone under the conversion conditions of ≤90 seconds;
   (d) recovering at least a portion of the product's aromatic hydrocarbon.

2. The process of claim 1, wherein the feed comprises ≥50 wt. % of $C_{2+}$ non-aromatic hydrocarbon, and wherein the $C_{2l}$ non-aromatic hydrocarbon comprises ≥75 wt. % of $C_2$-$C_4$ paraffinic hydrocarbon.

3. The process of claim 1, wherein (i) the catalyst includes ≥10 wt. % of the molecular sieve component and ≥0.005 wt. % of the dehydrogenation component, (ii) the molecular sieve component has a Constraint Index in the range of from 1-12, and (iii) the dehydrogenation component comprises one or more elements selected from Groups 3 to 13 of the Periodic Table.

4. The process of claim 1, wherein (i) the catalyst includes ≥25 wt. % of the molecular sieve component and ≥0.05 wt. % of the dehydrogenation component, (ii) the molecular sieve component comprises ≥90 wt. % of one or more of MCM-22, ZSM-5, ZSM-11, ZSM-12, ZSM-22, ZSM-23, ZSM-35, and ZSM-48, and (iii) the dehydrogenation component comprises ≥90 wt. % of one or more of Ga, Zn, Cu, Re, Mo, W, La, Fe, Ag, Pt, and Pd.

5. The process of claim 1, wherein the catalyst comprises ≥50 wt. % of the molecular sieve component and ≥1 wt. % of the dehydrogenation component, (ii) the molecular sieve component comprises ≥95 wt. % of H-ZSM-5, and (iii) ≥90 wt. % of the dehydrogenation component is Ga and/or Zn.

6. The process of claim 1, wherein the temperature is in the range of from 630° C. to 750° C., the pressure is in the range of from 30 psia (207 kPa) to 80 psia (522 kPa), the average residence time of the catalyst in the conversion zone under the conversion conditions is in the range of from 0.001 seconds to 60 seconds, and the conversion conditions include a GHSV is the range of from 1,100 $hr^{-1}$ to 40,000 $hr^{-1}$.

7. The process of claim 1, wherein the catalyst is in the form of a plurality of particles located in a turbulent bed, the bed having a density in the range of from 100 $kg/m^3$ to 500 $kg/m^3$ and a superficial fluid velocity in the range of 0.1 m/s to 10 m/s.

8. The process claim 7, wherein particles have an average size ≤250 μm and an average density in the range of from 0.6 $g/cm^3$ to 2 $g/cm^3$.

9. The process of claim 8, wherein (i) the average residence time of the catalyst particles in the conversion zone is in the range of from 0.01 seconds to 30 seconds, the bed volume is $V_B$, and (ii) the average residence time is achieved by
   (A) removing from the bed at least a portion of the catalyst particles at a rate in the range of 0.03 $V_B$/second to 100 $V_B$/second; and
   (B) introducing into the bed replacement catalyst particles in an amount sufficient to maintain the bed volume $V_B$ substantially constant during the conversion, the replacement catalyst particles having catalytic activity for dehydrocyclization of the $C_{2+}$ non-aromatic hydrocarbon, an average size ≤250 μm, and an average density in the range of from 0.6 $g/cm^3$ to 2 $g/cm^3$.

10. The process of claim 9, further comprising at least partially regenerating the removed catalyst particles, wherein ≥50 wt. % of the replacement catalyst particles comprise regenerated catalyst particles.

11. A natural gas upgrading process, comprising:
   (a) providing a feed which includes ≥50 wt. % of natural gas, the natural gas comprising $C_2$-$C_4$ paraffinic hydrocarbon;
   (b) providing a dehydrocyclization catalyst which includes (i) ≥25 wt. % of a molecular sieve component, the molecular sieve component comprising ≥90 wt. % of one or more of MCM-22, ZSM-5, ZSM-11, ZSM-12, ZSM-22, ZSM-23, ZSM-35, and ZSM-48, and (ii) ≥0.05 wt. % of a dehydrogenation component, the dehydrogenation component comprising ≥90 wt. % of one or more of Ga, Zn, Cu, Re, Mo, W, La, Fe, Ag, Pt, and Pd;
   (c) converting ≥65 wt. % of the feed's $C_2$-$C_4$ paraffinic hydrocarbon to a product comprising methane and ≥1 wt. % of aromatic hydrocarbon by exposing the feed to the dehydrocyclization catalyst in a reaction zone under dehydrocyclization conditions for an average residence time of the dehydrocyclization catalyst in the reaction zone under the dehydrocyclization conditions of ≤90 seconds, wherein the catalytic dehydrocyclization conditions include a temperature in the range of from 400° C. to 800° C., a pressure in the range of from 0 psig (101 kPa) to 300 psig (2170 kPa), and a space velocity (GHSV) ≥1100 hr$^{-1}$; and (d) recovering at least a portion of the product's aromatic hydrocarbon, wherein the conversion achieves an aromatic hydrocarbon selectivity ≥40 wt. % and a methane selectivity ≤40 wt. %.

12. The process of claim 11, wherein the (i) feed includes ≥90 wt. % of the natural gas, (ii) the $C_2$-$C_4$ hydrocarbon comprises 5 mole % to 50 mole % of ethane, 2 mole % to 40 mole % of propane, 0.1 mole % to 30 mole % of i-butane, and 1 mole % to 30 mole % of n-butane, and (iii) the feed comprises 0 mole % to 95 mole % of methane and 0.05 mole % to 25 mole % of i-pentane.

13. The process of claim 11, wherein the natural gas is an associated gas.

14. The process of claim 11, wherein (i) the dehydrogenation component comprises ≥95 wt. % of (A) Ga and/or (B) Zn, and (ii) the molecular sieve component comprises ≥95 wt. % of H-ZSM-5.

15. The process of claim 11, wherein the average residence time is in the range of from 0.01 seconds to 30 seconds, the temperature is in the range of from 630° C. to 750° C., the pressure is in the range of from 30 psia (207 kPa) to 80 psia (522 kPa), and the GHSV is in the range of from 1,500 hr$^{-1}$ to 40,000 hr$^{-1}$.

16. The process of claim 11, wherein the dehydrocyclization catalyst is in the form of a plurality of particles located in a turbulent bed, the bed having a density in the range of from 100 kg/m$^3$ to 500 kg/m$^3$ and a superficial fluid velocity in the range of 0.1 m/s to 10 m/s.

17. The process claim 16, wherein particles have an average size ≤250 μm and an average density in the range of from 0.6 g/cm$^3$ to 2 g/cm$^3$.

18. The process of claim 17, wherein (i) the average residence time is in the range of from 0.1 seconds to 10 seconds, the bed volume is $V_B$, and (ii) the average residence time is achieved by (A) removing from the bed at least a portion of the dehydrocyclization catalyst particles at a rate in the range of 0.1 $V_B$/second to 10 $V_B$/second; and (B) introducing into the bed replacement catalyst particles in an amount sufficient to maintain the bed volume $V_B$ substantially constant during the conversion, the replacement catalyst particles having catalytic activity for dehydrocyclization of the $C_2$-$C_4$ paraffinic hydrocarbon, an average size ≤250 μm, and an average density in the range of from 0.6 g/cm$^3$ to 2 g/cm$^3$.

19. The process of claim 18, further comprising at least partially regenerating the removed catalyst particles, wherein ≥90 wt. % of the replacement catalyst particles comprise regenerated catalyst particles.

20. A process for producing aromatic hydrocarbon, comprising:

(a) providing a feed comprising ≥1 wt. % of $C_{2+}$ non-aromatic hydrocarbon;

(b) providing a reaction zone which includes catalyst having catalytic activity for dehydrocyclization of the feed's $C_{2+}$ non-aromatic hydrocarbon, (c) reacting the feed's $C_{2+}$ non-aromatic hydrocarbon in a reaction zone in the presence of the catalyst under dehydrocyclization conditions to produce a product comprising methane and ≥1 wt. % of aromatic hydrocarbon, wherein (i) the dehydrocyclization conditions include a temperature in the range of from 400° C. to 800° C., a pressure in the range of from 0 psig (101 kPa) to 300 psig (2170 kPa), and a space velocity (GHSV) ≥1100 hr$^{-1}$, the dehydrocyclization catalyst having an average residence time in the reaction zone under the dehydrocyclization conditions of ≤90 seconds, and (ii) the reaction achieves (A) a $C_{2l}$ hydrocarbon conversion of X wt. % and (B) a methane selectivity of Y wt. %, and (iii) when (A) if X>60, then Y≤40, (B) if X is in the range of 50 to 60 then Y≤20, and (C) if X<50 then Y≤15; and (d) recovering at least a portion of the product's aromatic hydrocarbon.

21. The process of claim 20, wherein the feed comprises ≥90 wt. % ethane, with ≥95 wt. % of the balance of the feed comprising one or more of methane, propane, and butanes.

22. The process of claim 20, wherein the average residence time is in the range of from 0.01 seconds to 30 seconds, the temperature in the range of from 630° C. to 750° C., the pressure in the range of from 30 psia (207 kPa) to 80 psia (522 kPa), and the GHSV is in the range of from 1,500 hr$^{-1}$ to 40,000 hr$^{-1}$.

23. The process of claim 20, wherein the catalyst includes (i) ≥10 wt. % of a molecular sieve component, the molecular sieve component comprising ≥90 wt. % of one or more of MCM-22, ZSM-5, ZSM-11, ZSM-12, ZSM-22, ZSM-23, ZSM-35, and ZSM-48, and (ii) ≥0.005 wt. % of a dehydrogenation component, the dehydrogenation component comprising ≥90 wt. % of one or more of Ga, Zn, Cu, Re, Mo, W, La, Fe, Ag, Pt, and Pd.

24. The process of claim 23, wherein (i) the dehydrocyclization catalyst is substantially free of platinum, (ii) the dehydrogenation component comprises ≥95 wt. % of (A) Ga and/or (B) Zn, (iii) the molecular sieve component comprises ≥95 wt. % of H-ZSM-5;

(iv) the catalyst is in the form of a plurality of particles having an average size ≤250 μm and an average density in the range of from 0.6 g/cm$^3$ to 2 g/cm$^3$, the particles being located in a turbulent bed having volume $V_B$, a density in the range of from 100 kg/m$^3$ to 500 kg/m$^3$, and a superficial fluid velocity in the range of 0.1 m/s to 10 m/s;

(v) the average residence time is in the range of from 0.1 seconds to 10 seconds, (iv) the average residence time is achieved by:

(A) removing from the bed at least a portion of the catalyst particles at a rate in the range of 0.1 $V_B$/second to 10 $V_B$/second; and (B) introducing into the bed replacement catalyst particles in an amount sufficient to maintain the bed volume $V_B$ substantially constant during the conversion, the replacement catalyst particles having catalytic activity for dehydrocyclization of the feed's $C_{2+}$ non-aromatic hydrocarbon, an average size ≤250 μm, and an average density in the range of from 0.6 g/cm$^3$ to 2 g/cm$^3$.

25. The process of claim 20, further comprising alkylating at least a portion of the aromatic product to produce toluene and/or xylene.

* * * * *